United States Patent
Hyun et al.

(10) Patent No.: US 11,030,780 B2
(45) Date of Patent: Jun. 8, 2021

(54) ULTRASOUND SPECKLE REDUCTION AND IMAGE RECONSTRUCTION USING DEEP LEARNING TECHNIQUES

(71) Applicant: The Board of Trustees of the Leland Stanford Junior University, Stanford, CA (US)

(72) Inventors: Dongwoon Hyun, Sunnyvale, CA (US); Jeremy J. Dahl, Palo Alto, CA (US); Kevin T. Looby, Stanford, CA (US); Leandra L. Brickson, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 25 days.

(21) Appl. No.: 16/365,175

(22) Filed: Mar. 26, 2019

(65) Prior Publication Data
US 2019/0295295 A1    Sep. 26, 2019

Related U.S. Application Data

(60) Provisional application No. 62/648,009, filed on Mar. 26, 2018.

(51) Int. Cl.
| | |
|---|---|
| *G06T 11/00* | (2006.01) |
| *G06N 3/08* | (2006.01) |
| *G06N 20/00* | (2019.01) |
| *A61B 8/08* | (2006.01) |

(52) U.S. Cl.
CPC .......... *G06T 11/008* (2013.01); *A61B 8/5207* (2013.01); *A61B 8/5215* (2013.01); *G06N 3/08* (2013.01); *G06N 20/00* (2019.01); *G06T 2211/428* (2013.01)

(58) Field of Classification Search
None
See application file for complete search history.

(56) References Cited

U.S. PATENT DOCUMENTS 9,275,471 B2 * 3/2016 Hamilton ................. G06T 7/246
10,879,609 B1 * 12/2020 Judd ..................... F41H 13/0075

(Continued)

OTHER PUBLICATIONS

Mishra, Deepak, Santanu Chaudhury, Mukul Sarkar, and Arvinder Singh Soin. "Ultrasound image enhancement using structure oriented adversarial network." IEEE Signal Processing Letters 25, No. 9 (2018): 1349-1353. (Year: 2018).*

(Continued)

*Primary Examiner* — Michelle M Entezari
(74) *Attorney, Agent, or Firm* — Lumen Patent Firm

(57) ABSTRACT

Ultrasound B-mode images are reconstructed directly from transducer channel signals using a convolutional neural network (CNN). The CNN is trained with a dataset including, as inputs, simulated transducer array channel signals containing simulated speckle and, as outputs, corresponding simulated speckle-free B-mode ground truth images. After training, measured real-time RF signals taken directly from an ultrasound transducer array elements prior to summation are input to the CNN and processed by the CNN to generate as output an estimated real-time B-mode image with reduced speckle.

11 Claims, 10 Drawing Sheets

(56) References Cited

U.S. PATENT DOCUMENTS

| | | | |
|---|---|---|---|
| 2003/0028107 A1* | 2/2003 | Miller | A61B 8/12 |
| | | | 600/437 |
| 2005/0075791 A1* | 4/2005 | Lailly | G01V 1/36 |
| | | | 702/17 |
| 2005/0154304 A1* | 7/2005 | Robinson | G01S 7/52028 |
| | | | 600/443 |
| 2016/0350620 A1 | 12/2016 | Rao | |
| 2017/0046616 A1* | 2/2017 | Socher | G06K 9/4628 |
| 2018/0143165 A1* | 5/2018 | Dahl | G01N 29/024 |
| 2018/0177461 A1* | 6/2018 | Bell | A61B 5/7267 |
| 2019/0030370 A1* | 1/2019 | Hibbard | G16H 20/40 |
| 2020/0167930 A1* | 5/2020 | Wang | G06T 7/0012 |

OTHER PUBLICATIONS

Dietrichson, F., Smistad, E., Ostvik, A., & Lovstakken, L. (Oct. 2018). Ultrasound speckle reduction using generative adversial networks. In 2018 IEEE International Ultrasonics Symposium (IUS) (pp. 1-4). IEEE. (Year: 2018).*

Bottenus, N., Le Fevre, M., Cleve, J., Crowley, A. L., & Trahey, G. (2020). Resolution and Speckle Reduction in Cardiac Imaging. IEEE Transactions on Ultrasonics, Ferroelectrics, and Frequency Control. (Year: 2020).*

Hyun, D., Brickson, L. L., Looby, K. T., & Dahl, J. J. (2019). Beamforming and speckle reduction using neural networks. IEEE transactions on ultrasonics, ferroelectrics, and frequency control, 66(5), 898-910. (Year: 2019).*

Vedula, S., et al., "Towards CT-quality Ultrasound Imaging using Deep Learning" arXiv:1710.06304v1 [cs.CV] Tue, Oct. 17, 2017.

* cited by examiner

ULTRASOUND SPECKLE REDUCTION AND IMAGE RECONSTRUCTION USING DEEP LEARNING TECHNIQUES

CROSS-REFERENCE TO RELATED APPLICATIONS

This application claims priority from U.S. Provisional Patent Application 62/648,009 filed Mar. 26, 2018, which is incorporated herein by reference.

STATEMENT REGARDING FEDERALLY SPONSORED RESEARCH OR DEVELOPMENT

This invention was made with Government support under contract EB015506 awarded by the National Institutes of Health. The Government has certain rights in the invention.

FIELD OF THE INVENTION

The invention relates generally to ultrasound imaging. More specifically, it relates to techniques for reducing artifacts in ultrasound image reconstruction.

BACKGROUND OF THE INVENTION

In brightness mode (B-mode) ultrasound imaging, the echoes from an ultrasonic pulse are used to reconstruct images according to their magnitude (i.e. brightness). Thus, B-mode images are a map of the echogenicity of the insonified medium. The echo magnitudes are measured using an array of sensors via a process referred to as beamforming. The classical beamformer is delay-and-sum (DAS), which forms a point-wise estimate of echogenicity based on the magnitude of the summed array signals.

However, in medical ultrasound imaging, echoes are generated by scattering sources that are smaller than the resolution of the imaging system. These echoes from sub-resolution scatterers interfere stochastically, producing a strong multiplicative noise in the measured DAS output. This noise is referred to as speckle. Speckle manifests as a temporally stationary grainy texture in regions with homogeneous echogenicity. Speckle is commonly used to infer the scattering properties of tissue and can be used for tracking blood flow and tissue displacements. However, for the task of echogenicity estimation, speckle reduces the perceived resolution of the target and is largely treated as an undesirable noise that degrades diagnostic B-mode imaging.

Speckle reduction can be accomplished using beamforming methods that operate on the radiofrequency signals received by an array of transducer elements, or by post-processing techniques that filter images after they are reconstructed.

Common beamforming techniques for speckle reduction are designed according to the underlying physics and statistics of speckle. These techniques include spatial and frequency compounding, in which the aperture or the bandwidth are subdivided, respectively. These subdivisions are used independently to reconstruct images that are subsequently averaged. The overall speckle is reduced because the speckle patterns observed by each subdivision are decorrelated from one another.

Spatial compounding uses independently-beamformed subapertures to observe the target from multiple angles, reducing speckle at the cost of lateral resolution. However, improvements in speckle SNR are limited to $\sqrt{N}$ when spatial compounding with N uncorrelated images, with lesser improvements when the compounded images are correlated.

In addition, beamforming has historically been viewed as a method of suppressing off-axis noises or improving resolution, rather than a means for speckle reduction. Examples of other beamformers include minimum variance beamforming, in which the channels are weighted to suppress off-axis noises, as well as a newly proposed machine learning method in which deep fully connected networks are used to filter signals arriving from outside of the main lobe. In these cases, beamforming is used to preserve speckle, rather than to remove it.

Speckle reduction has been studied far more extensively in the context of post-processing filters, which are applied to images that have already been beamformed. Popular techniques include anisotropic diffusion and discrete wavelet transforms. A stochastic iterative technique to remove pixel outliers, called the squeeze box filter, has also been proposed. More recently, non-local means methods have demonstrated excellent speckle reduction capabilities. These techniques selectively smooth pixels originating from speckle while preserving other structures and details. However, a disadvantage to purely post-processing techniques is that they rely entirely on fully-formed images of demodulated and envelope detected data, and are thus unable to take advantage of channel and phase information that are irreversibly lost in the summation and image formation process, respectively.

OBNLM is a post-processing technique that excels at preserving sharp discontinuities and point targets. However, OBNLM has problems maintaining resolution and target structure for broader targets and gradual changes in echogenicity. OBNLM also utilizes three parameters which must be tuned precisely to achieve the desired speckle reduction. The known parameters, however, are inadequate for some in vivo imaging cases. Moreover, as a post-processing method, OBNLM is fundamentally subject to any noise artifacts that are present in the envelope-detected DAS image.

BRIEF SUMMARY OF THE INVENTION

In one aspect, the present invention provides a method for ultrasound image reconstruction using a neural network. A method is provided for reconstructing speckle-reduced B-mode images directly from real-time ultrasound channel signals using a convolutional neural network. This technique significantly outperforms delay-and-sum and receive-only spatial compounding in speckle reduction while preserving resolution and exhibited improved detail preservation over a non-local means methods.

Ultrasound B-image reconstruction with neural networks represents a fundamentally different paradigm for speckle reduction as compared to traditional techniques. It is an array processing technique that performs reconstruction and speckle reduction in tandem using parameters that are learned, nonlinearly transforming complex channel data into echogenicity estimates.

A convolutional neural network (CNN) is trained with simulated RF transducer array channel signals containing simulated speckle and corresponding ground-truth speckle-free echogenicity images. The CNN then estimates real-time B-mode (echogenicity) images from measured real-time RF signals taken directly from ultrasound transducer array elements (prior to summation).

Supervised learning with neural networks is a class of machine learning techniques in which a cascade of transformations are applied to an input in order to eventually produce a desired output. The parameters of the transformation are learned via a gradient descent algorithm designed to minimize the error between the output of the network and the known ground truth.

A neural networks in this invention is trained to reconstruct speckle-reduced B-mode images by being presented with many instances of ultrasound transducer channel data and corresponding ground truth speckle-free B-mode images. Such training has been difficult to implement in the past partly because ground truth echogenicity is virtually unavailable in vivo. Ground truth can be obtained in simulations, but it was not previously known whether a network trained entirely in silico can generalize to real-world imaging conditions such as in vivo, where ultrasound signals face additional challenges via image degradation such as phase aberration, acoustical noise, and electronic noise.

According to techniques of the present invention, linear simulations of ultrasound imaging in conjunction with deep convolutional neural networks are used to empirically learn speckle-reducing B-mode image reconstruction. Neural networks can be trained to transform ultrasound transducer channel data, before summation, directly into B-mode images. Deep neural networks are trained using simulated ultrasound channel data that are co-registered with a reference ground truth map of echogenicity.

In addition to suppressing noise from outside the intended focus, an ideal beamformer for B-mode imaging according to the teachings of the present invention should be an estimate of the average echogenicity of the scatterers. In particular, the backscatter from a homogeneous region of tissue of constant echogenicity should produce a uniform response (as opposed to a speckle response) while preserving the structure and echogenicity of the medium.

Embodiments of the invention may include the use of two ultrasound-appropriate modifications to the $l_1$, $l_2$, and MS-SSIM loss functions. First, the loss functions are measured on logarithmically compressed images to account for the large dynamic range of ultrasound signals and to match the log-domain in which the images were displayed. Second, a normalization-independent formulation of the loss function is used to compare two images with arbitrary units.

In one aspect, the invention provides a method for ultrasound image reconstruction using a convolutional neural network (CNN). The method includes training the CNN with a dataset comprising simulated transducer array channel signals containing simulated speckle as inputs, and corresponding simulated speckle-free B-mode images as outputs; measuring real-time RF signals taken directly from ultrasound transducer array elements prior to summation; inputting the measured real-time RF signals to the CNN; and processing by the CNN the measured real-time RF signals to produce as output an estimated real-time B-mode image with reduced speckle. The estimated B-mode images are estimated by the CNN from the simulated transducer array channel signals. The training uses a loss function involving a norm between estimated B-mode images and simulated speckle-free B-mode images. For example, the loss function may be a log-domain normalization-independent loss function, or a normalization-independent mixture of $l_1$ and multi-scale structural similarity losses. The simulated transducer array channel signals may be unfocused or focused channel signals. The input signals may be modulated RF signals or demodulated baseband signals. The CNN preferably has 8 to 16 convolution blocks, wherein each of the convolution blocks has a 2D convolution, batch normalization, and a rectified linear unit. Preferably, the CNN has 16 layers of convolution blocks and 32 filters per layer. The CNN preferably concatenates the original input data to an intermediate hidden layer of the network. Preferably, the CNN performs a multi-scale or multi-resolution processing of the data via striding or pooling. The CNN in some embodiments may include 3D convolutions. The method may also include performing a conventional DAS envelope-detection reconstruction to generate a conventional B-mode image from the real-time RF signals, and concatenating the generated conventional B-mode image to an output of a block of the CNN.

BRIEF DESCRIPTION OF THE SEVERAL VIEWS OF THE DRAWINGS

FIGS. 3A, 3B, 3C show neural networks with 2, 4, 8, or 16 layers of convolution blocks and 32 filters per layer, and FIGS. 3D, 3E, 3F show neural networks with 16 layers of convolution blocks and 4, 8, 16, or 32 filters per layer, according to an embodiment of the invention.

FIG. 6A shows a 2 mm anechoic cyst and a 8 mm −12 dB cyst. FIG. 6A shows a 8 mm+12 dB cyst and several bright point targets.

DETAILED DESCRIPTION OF THE INVENTION

Problem Formulation

Consider a vectorized grid of P×Q field points (also referred to as "pixels") with true echogenicities $y \in \mathbb{R}^{PQ}$. Let $X \in \mathbb{C}^{PQ \times N}$ denote the demodulated analytic signals captured by the N elements of a transducer array after applying the appropriate time delays to focus the array at each of the field points. In B-mode image reconstruction, y is estimated from X using some function $f(X) = \hat{y}$.

Figure 1A:
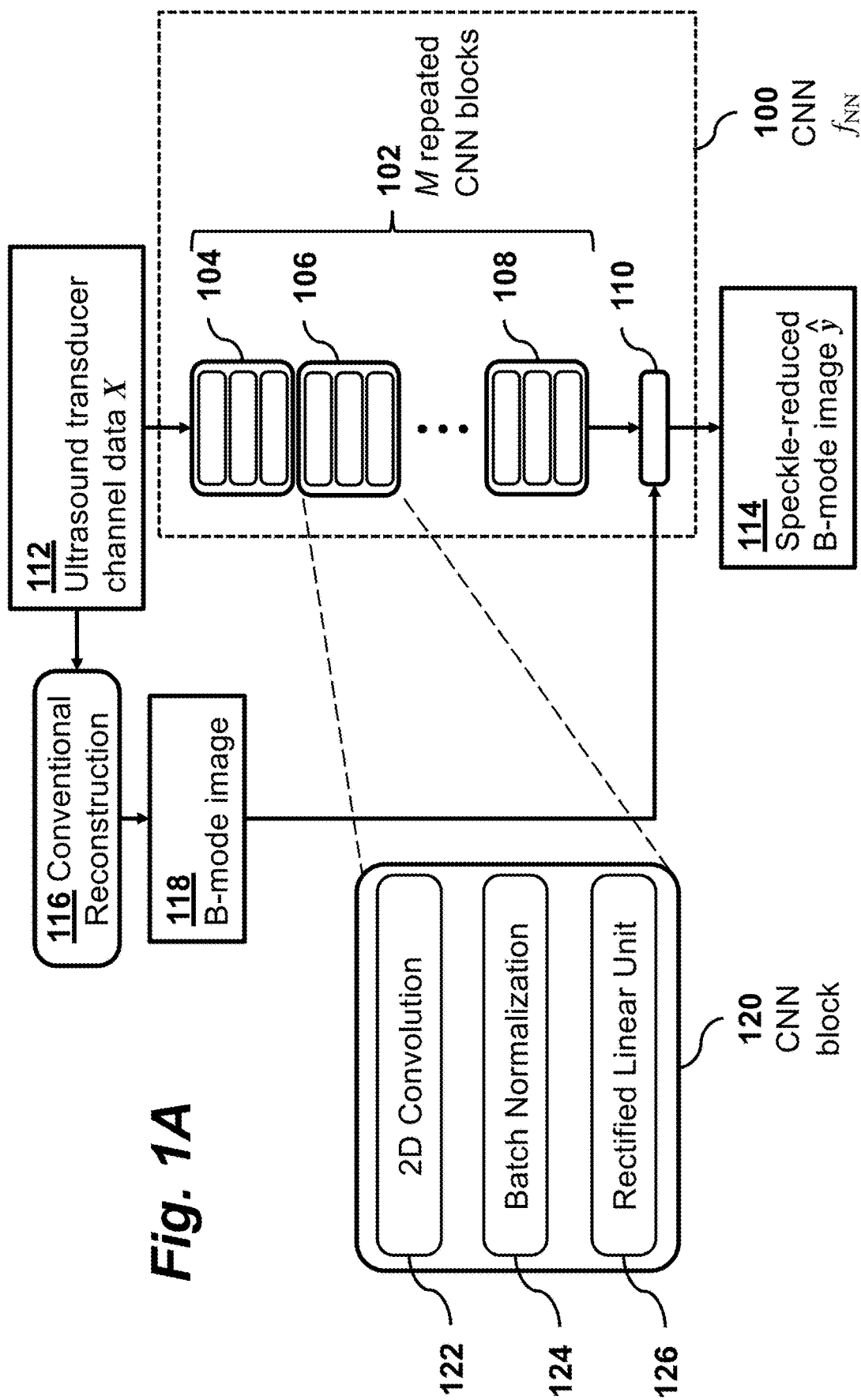
FIG. 1A is a schematic diagram illustrating the processing pipeline for image reconstruction, including details of the architecture of a fully convolutional neural network according to an embodiment of the invention, where the network has a sequence of M convolution blocks, each having a 2D convolution, batch normalization, and a rectified linear unit.

In the traditional delay-and-sum (DAS) technique, y is estimated as the absolute value of the channel sum:

$$\hat{y} = f_{DAS}(X) = |X\mathbf{1}|, \quad (1)$$

where 1 is an N-vector of ones and |•| denotes an element-wise absolute value. According to the present invention, y is estimated by a convolutional neural network using a function $f_{NN}(X; \theta)$, where $\theta$ are the parameters of the network. As illustrated in FIG. 1A, the estimate $\hat{y} = f_{NN}(X; \theta)$ is computed by a convolutional neural network 100 that takes the ultrasound transducer data 112 as its input X and produces a speckle-reduced B-mode image 114 as its output $\hat{y}$.

In order to reconstruct desired B-mode images with a neural network, the network 100 is first trained using training data, i.e., a set of inputs and corresponding true outputs that can be compared to the network output using a loss function. The training process is designed to determine the optimal parameters $\theta^*$ that minimize the error between an estimated image y output from the network and the true image y, as quantified by some loss function $\mathcal{L}(y, \hat{y})$:

$$\theta^* = \underset{\theta}{\operatorname{argmin}}\, \mathcal{L}(y, f_{NN}(X; \theta)). \quad (2)$$

The minimization problem is typically solved using some form of gradient descent, an approach in which each of the parameters is iteratively updated to reduce the error:

$$\theta_j := \theta_j - \alpha \frac{\partial}{\partial \theta_j} \mathcal{L}(y, f_{NN}(X; \theta)), \quad (3)$$

where α denotes the step size, also called the learning rate.

Standard Loss Functions The choice of loss function significantly affects the training process. The $l_1$ and $l_2$ norms are often used to quantify the reconstruction error:

$$\mathcal{L}_{\ell_1}(y, \hat{y}) = \frac{1}{PQ} \sum_{p=1}^{PQ} |y_p - \hat{y}_p| \quad (4)$$

$$\mathcal{L}_{\ell_2}(y, \hat{y}) = \left(\frac{1}{PQ} \sum_{p=1}^{PQ} (y_p - \hat{y}_p)^2 \right)^{\frac{1}{2}}, \quad (5)$$

where the p-th pixels of y and $\hat{y}$ are respectively denoted as $y_p$ and $\hat{y}_p$. Alternative metrics such as structural similarity (SSIM) and multi-scale structural similarity (MS-SSIM) have also been proposed. The SSIM between pixels $y_p$ and $\hat{y}_p$ is computed as $$SSIM(y_p - \hat{y}_p) = \left(\frac{2\mu_{y_p}\mu_{\hat{y}_p} + C_1}{\mu_{y_p}^2 + \mu_{\hat{y}_p}^2 + C_1}\right)\left(\frac{2\sigma_{y_p\hat{y}_p} + C_2}{\sigma_{y_p}^2 + \sigma_{\hat{y}_p}^2 + C_2}\right), \quad (6)$$

where $C_1$ and $C_2$ are empirically selected scalar parameters to enhance numerical stability, $\mu_{y_p}$ and $\mu_{\hat{y}_p}$ are the mean values of a neighborhood around $y_p$ and $\hat{y}_p$, respectively, $\sigma_{y_p}^2$ and $\sigma_{\hat{y}_p}^2$ are their variances, and $\sigma_{y_p\hat{y}_p}$ is their covariance. The means, variances, and covariance are obtained using Gaussian filters. SSIM values range from −1 to 1, where 1 indicates perfect correspondence between the images. Therefore, a loss function can be defined as $$\mathcal{L}_{SSIM}(y, \hat{y}) = 1 - \frac{1}{PQ} \sum_{p=1}^{PQ} SSIM(y_p - \hat{y}_p). \quad (7)$$

The $\mathcal{L}_{MS\text{-}SSIM}$ metric extends SSIM by combining $\mathcal{L}_{SSIM}$ measurements using several neighborhood sizes in order to compare the images at multiple resolution scales. The different scales can be achieved either by downsampling the image or by changing the standard deviation parameter of the Gaussian filter. In this work, we adopt the latter approach.

Loss Functions for Ultrasound B-Mode Imaging

In B-mode imaging, it is important to accurately reconstruct hypoechoic targets such as blood vessels and heart chambers, whose signals can be more than 40 dB (100 times) weaker than the background tissue. B-mode images are typically compressed prior to being viewed in order to visualize the wide dynamic range. However, the large discrepancy in signal strengths may cause standard loss functions to over-emphasize errors in strongly echogenic targets and to under-emphasize errors in hypoechoic targets. Therefore, we propose to compute losses using logarithmically compressed images, i.e., $\mathcal{L}(\log y, \log \hat{y})$. This allows the errors to be measured in the same domain that the images are viewed in.

Another challenge is that B-mode images and their ground truth echogenicity maps are both defined in arbitrary units, making it unclear how to compare the two images. One approach is to normalize each respective image, (e.g., by their maximum values). Unfortunately, the standard loss functions are highly sensitive to the normalization, whereas an ideal loss function for images with arbitrary units should be independent of their normalization.

Preferred embodiments of the invention use a new loss function that is intrinsically independent of normalization and is suitable for comparing two images with arbitrary units. Let $\mathcal{L}^*$ define the minimum achievable loss $\mathcal{L}$ when $\hat{y}$ is scaled by some positive weight parameter w:

$$\mathcal{L}^*(\log y, \log \hat{y}) = \min_{w>0} \mathcal{L}(\log y, \log w\hat{y}). \quad (8)$$

These loss functions apply precise normalization to each image such that the $\mathcal{L}_1$, $\mathcal{L}_2$, and $\mathcal{L}_{MS\text{-}SSIM}$ losses are minimized, respectively, allowing the images to be compared according to their relative contrasts and structures rather than their absolute magnitudes.

Closed form expressions for the $\mathcal{L}^*_{l_1}$, $\mathcal{L}^*_{l_2}$, and $\mathcal{L}^*_{MS\text{-}SSIM}$ loss functions are provided as follows:

The $\mathcal{L}^*_{l_2}$ Loss Function

The optimal weight for the $l_2$-norm is found as:

$$w^*_{\ell_2} = \operatorname*{argmin}_{w>0} \|y - w\hat{y}\|_2 \quad (9)$$

$$= \operatorname*{argmin}_{w>0} w^2 \hat{y}^T \hat{y} - 2w\hat{y}^T y. \quad (10)$$

The optimum value can be found by taking the derivative with respect to w and solving for the minimum, giving $$w^*_{\ell_2} = \frac{\hat{y}^T y}{\hat{y}^T \hat{y}}. \quad (11)$$

The $\mathcal{L}^*_{l_1}$ Loss Function

The optimal weight for the $l_1$-norm is obtained as:

$$w^*_{\ell_1} = \operatorname*{argmin}_{w>0} \sum_{p=1}^{P} \left| w - \frac{y_p}{\hat{y}_p} \right|. \quad (12)$$

The minimum, where the derivative with respect to w is zero, can be found by using the relation $$\frac{\partial}{\partial w} |w - u| = \operatorname{sign}(w - u), \quad (13)$$

yielding an optimal solution that is the median value of $y_p/\hat{y}_p$:

$$0 = \sum_{p=1}^{P} \operatorname{sign}\left( w^*_{\ell_1} - \frac{y_p}{\hat{y}_p} \right) \quad (14)$$

$$w^*_{\ell_1} = \operatorname{median}\left\{ \frac{y_p}{\hat{y}_p} \right\}_{p=1}^{P}. \quad (15)$$

The $\mathcal{L}^*_{MS\text{-}SSIM}$ Loss Function

The SSIM metric is the product of the differences in luminance, contrast, and structure, which correspond to differences in the mean, standard deviation, and the normalized signals, respectively. When computed on log-images, the optimal weight is additive. In the case of the SSIM, we find that the derivative with respect to w for one pixel p is $$\frac{\partial}{\partial w} SSIM(\log y_p, w + \log \hat{y}_p) = \quad (16)$$

$$\frac{4\mu_{\log y_p} \sigma^2_{\log y_p \log \hat{y}_p} (\mu^2_{\log y_p} - (w + \mu_{\log \hat{y}_p})^2)}{(\sigma^2_{\log y_p} + \sigma^2_{\log \hat{y}_p})(\mu^2_{\log y_p} + (w + \mu_{\log \hat{y}_p})^2)^2}, \quad (17)$$

where the stabilizing constants $C_1$ and $C_2$ are omitted. The optimal weight is obtained by solving for w over all pixels:

$$0 = \sum_{p=1}^{P} \frac{\partial}{\partial w} SSIM(\log y_p, w + \log \hat{y}_p). \quad (18)$$

Unfortunately, this equation is intractable for large P.

We instead utilize a (potentially suboptimal) weight:

$$w^* = \frac{1}{PQ} \sum_{p=1}^{PQ} \log y_p - \frac{1}{PQ} \sum_{p=1}^{PQ} \log \hat{y}_p. \quad (19)$$

This is equivalent to computing the SSIM without the luminance term:

$$SSIM^*(\log y_p, \log \hat{y}_p) = \frac{1}{PQ} \sum_{p=1}^{PQ} \frac{2\sigma^2_{\log y_p \log \hat{y}_p} + C_2}{\sigma^2_{\log y_p} + \sigma^2_{\log \hat{y}_p} + C_2}. \quad (20)$$

Similarly, the multi-scale luminance-independent MS-SSIM loss function is then defined as $$\mathcal{L}^*_{MS\text{-}SSIM}(\log y, \log \hat{y}) = 1 - \prod_j SSIM^*_j(\log y, \log \hat{y}), \quad (21)$$

where j indexes the scales over which the SSIM* is computed.

Field II Simulation Training Dataset

The network 100 is preferably trained using simulated ultrasound data. For example, in one embodiment, the Field II Pro simulation package was used to simulate ultrasound channel data from 128 elements of a Verasonics L12-3v linear array transducer. A full synthetic aperture data set was simulated using single-element transmits at 8 MHz with 60% bandwidth. Speckle was simulated with random uniformly distributed scatterers in a 10 mm×10 mm×3 mm phantom centered at the elevation focus of 2 cm. The scatterer density was selected to be 60 scatterers per resolution cell, and the scattering amplitudes were normally distributed and weighted according to ground truth echogenicity maps.

To provide the network with a wide range of features and contrasts, real photographic images were used as the ground truth echogenicity. The images were taken from publicly available image databases: 512 images from a Places2 test set and 512 images from an ImageNet validation set were selected for a total of 1024 images. These images were used solely for their patterns and contrasts; their corresponding classification labels were not used. The images were converted to grayscale and cropped into a 224 pixel×224 pixel square patch. The patch was then mapped onto the lateral and axial extent of the phantom (10 mm×10 mm) to serve as the ground truth echogenicity map, and the pixel intensities were used to weight the scattering amplitudes of the simulated scatterers according to their positions via bilinear interpolation. This approach was chosen as a convenient alternative to custom-designing a wide variety of ground truth echogenicity maps.

For each of the 1024 images, an independent set of random scatterers was weighted and used in a full synthetic aperture simulation. For each simulation, the received radiofrequency (RF) channel signals were demodulated and focused into the same 224 pixel×224 pixel grid as the ground truth echogenicity map, with dynamic focusing applied on both transmit and receive. The dimensions of the resulting data cube were 224 pixels×224 pixels×128 channels.

The set of 1024 simulations was then resampled to generate an augmented training dataset comprised of 5000 co-registered pairs of focused channel data and reference ground-truth echogenicity. The resampled data/reference pairs were selected to have a smaller patch size of 64 pixels×64 pixels and each was drawn randomly from one of the 1024 simulations. While the number of pixels was held constant, the lateral and axial positions and sizes of the patches were allowed to vary independently of one another, resulting in rectangular patches. The resulting 64×64 patches were then treated as though they were square patches with stretched speckle patterns, enabling the emulation of a wide variety of imaging configurations from a limited number of simulations. Each channel dataset was corrupted by a random amount of white thermal noise and band-limited acoustical reverberation noise, specified in decibels (dB) relative to the RMS of the channel signals. Each attribute was selected randomly from a uniform distribution over the range of values listed in Table 1.

TABLE 1

Range of Parameters for Random Patches

| Attribute | Minimum Value | Maximum Value |
| --- | --- | --- |
| Simulation Index | 1 | 1024 |
| Lateral Position | −1.9 mm (−10λ) | 1.9 mm (10λ) |
| Axial Position | 18.1 mm (94λ) | 21.9 mm (114λ) |
| Lateral Size | 0.4 mm (2λ) | 6.2 mm (32λ) |
| Axial Size | 0.4 mm (2λ) | 6.2 mm (32λ) |
| Thermal Noise | −40 dB | +6 dB |
| Acoustical Noise | −40 dB | +6 dB |

Image Reconstruction Quality Metrics

The quality of image reconstruction was measured using several metrics. The $\mathcal{L}^*_{l_1}$, $\mathcal{L}^*_{l_2}$, and $\mathcal{L}^*_{MS\text{-}SSIM}$ errors were computed between the reconstructed log-image and the ground truth echogenicity log-image when available. The $\mathcal{L}^*_{l_2}$ and $\mathcal{L}^*_{l_1}$ errors were obtained in units of dB, whereas the $\mathcal{L}^*_{MS\text{-}SSIM}$ error was bounded from 0 to 2, with 0 being achieved when y=ŷ. The reconstruction quality was also measured using the contrast and contrast-to-noise ratio (CNR) of cyst targets and using the signal-to-noise ratio (SNR) of the tissue background:

$$\text{Contrast} = 20 \log_{10}\left(\frac{\mu_t}{\mu_b}\right) \quad (22)$$

$$CNR = \frac{\mu_t - \mu_b}{\sqrt{\sigma_t^2 + \sigma_b^2}} \quad (23)$$

$$SNR = \frac{\mu_b}{\sigma_b}, \quad (24)$$

where $\mu_t$ and $\mu_b$ denote the means and $\sigma_t$ and $\sigma_b$ the standard deviations of the target and background, respectively. Contrast, CNR, and SNR were computed on the linear scale images, prior to log-compression. The CNR essentially combines the contrast and SNR metrics into a single measure of lesion detectability. In the simulations and the phantom, the cyst contrasts and CNRs were measured in concentric regions of interest (ROIs). The target ROI was selected as a circle with a radius of 0.8 times the cyst radius, and the background ROI as a ring with inner and outer radii of 1.1 and 1.5 times the cyst radius, respectively. The background SNR was measured in a homogeneous region of speckle. For DAS beamforming, the measured pixel values in a region of homogeneous echogenicity are classically expected to follow the Rayleigh distribution, resulting in an SNR of 1.91.

Image resolution was measured using the following methodology. First, the system response to a transition between two regions of different echogenicities was measured, referred to as the edge spread function (ESF). Field II Pro was used to simulate a target wherein half the azimuthal field of view was a speckle region of constant echogenicity and the other half was an anechoic region. The resulting images were averaged axially and over 16 independent scatterer realizations to reduce noise. Next, the ESF was differentiated in the azimuthal dimension to produce a line spread function (LSF). Finally, the FWHM of the LSF was measured to obtain the image resolution.

Deep Convolutional Neural Networks

Convolutional neural networks were used to estimate echogenicity from the focused and demodulated channel signals. Analysis was restricted to a maximum of 16 channels per pixel due to computational and memory constraints. To achieve this, the 128 element array was subdivided into 16 equal subapertures of 8 elements each, and the signals from each subaperture were beamformed into a single signal, yielding a total of 16 complex signals per pixel. The real and imaginary components were then concatenated in the channel dimension prior to being input into the neural network, resulting in 32 distinct channels per pixel, i.e., for a pixel grid of size P×Q, the resulting data was P×Q×32.

The network architecture 100 is shown in FIG. 1A. The network 100 has a sequence of M repeated convolution blocks 102, with each block 104, 106, 108 applying a 2D convolution 122, batch normalization 124, and rectified linear unit activation 126. This motif was repeated for all M blocks in the sequence 102. Each 2D convolution layer 122 was composed of F machine-learned filters, and the size of each filter was 7×7×32 for the first layer, 5×5×F for the second layer, and 3×3×F for subsequent layers, with the convolution occurring over the first two dimensions of each. Each convolution was zero-padded in the first two dimensions such that the input and output were the same size, making the size of the output of each convolutional layer P×Q×F.

The input to the network was a 64×64×32 dataset, where the last dimension corresponded to real and imaginary components of 16 subaperture signals. A conventional DAS envelope-detection reconstruction 116 generates a conventional B-mode image 118, which was concatenated to the output of the M-th block 108. The speckle-reduced B-mode image output 114 was obtained by applying one final 2D convolution 110 and squaring the result. As will be explained further below in relation to FIGS. 4A-C, concatenating the B-mode image 118 after the M-th convolutional block significantly enhances training. Although the input channel data 112 theoretically contain all of the raw information necessary to reconstruct a B-mode image 114, it appears that the concatenated B-mode image 118 served as a good initial estimate of echogenicity for the network to improve upon, rather than learning the reconstruction from scratch. The uncompressed B-mode image 118 is separately formed from the input data 112 using equation (1) and concatenated to the output of the M-th block 108, yielding a data array of size P×Q×(F+1). The final convolution filter 110 of size 1×1×(F+1) was used to produce the output image 114 of size P×Q×1 that was subsequently squared on a pixel-wise basis to yield positive values of echogenicity. The fully convolutional nature of the network allowed echogenicity estimation on a pixel-wise basis. Unless otherwise specified, the default parameters for the networks were M=16 convolution blocks with F=32 filters per layer. Pooling layers and dropout were not utilized.

In an alternative configuration, the original input is concatenated to the output of one or more of the intermediate blocks instead of the B-mode image, yielding a data array size of 1×1×2F instead of 1×1×(F+1). Any subsequent convolution filters would have the appropriate size (i.e., 2F) to accommodate the new data size. In a different configuration, the network an encoding-decoding structure is used to achieve multi-scale or multi-resolution processing, in which intermediate encoding layers apply pooling or striding, i.e., reduce the data dimensions in the first two dimensions by some factor D, and subsequent intermediate decoding layers increase the data dimensions in the first two dimensions by the same factor D; intermediate layers may be connected via concatenation. In another configuration, the 2D convolution layers are replaced by 3D convolutions that additionally convolve in the transducer channel dimension. In this configuration, the real and imaginary components of the data are preserved as a separate dimension from the channel signals, such that the data size is 64×64×16×2.

Figure 1B:
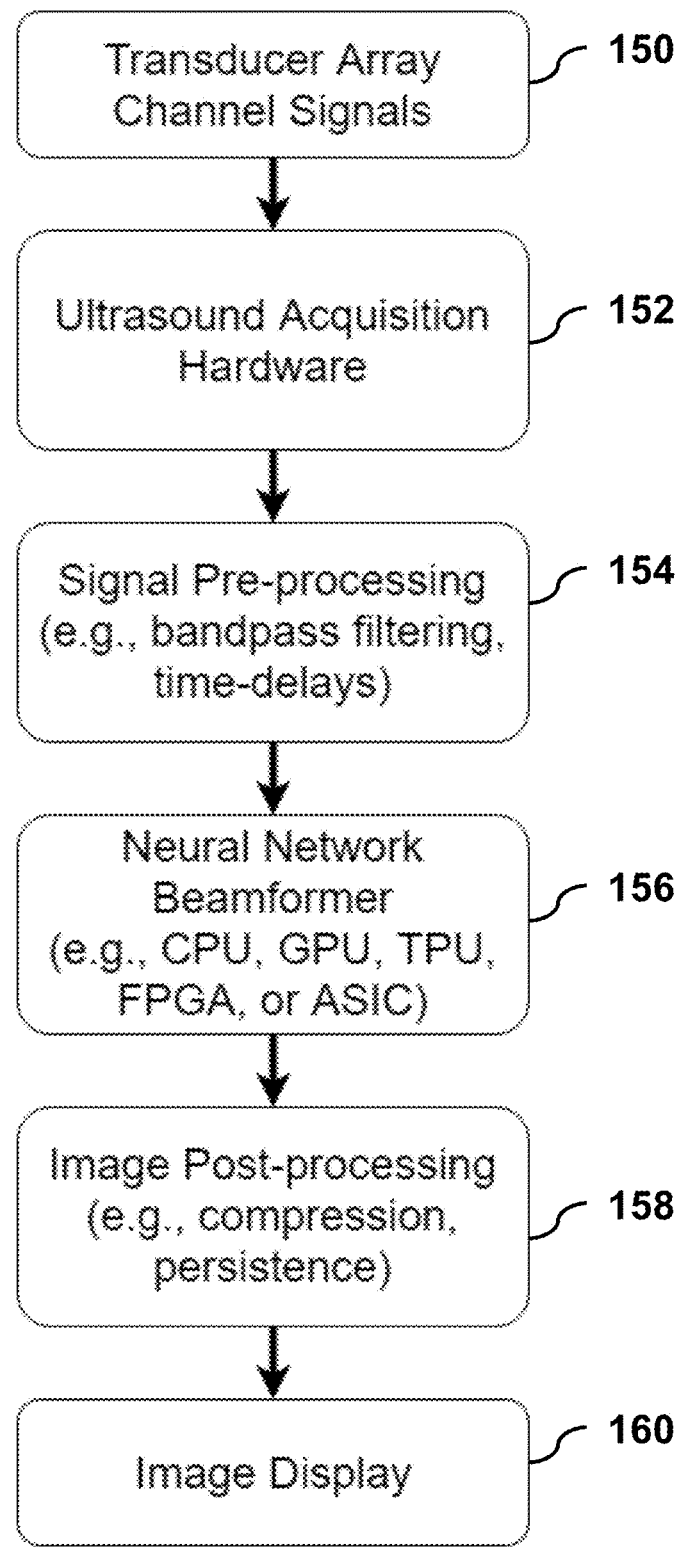
FIG. 1B is a flow diagram illustrating an overview of major components of an apparatus for image reconstruction according to an embodiment of the invention.

FIG. 1B provides an overview of major components of an apparatus for image reconstruction according to an embodiment of the invention. Transducer array channel signals 150 output from an ultrasound transducer array are provided to ultrasound acquisition hardware 152 which sample, amplify, and digitize the radiofrequency channel signals, which are then provided to signal pre-processing component 154 which performs bandpass filtering, time delays, and demodulation. The pre-processed signals are then input to neural network beamformer 156. The neural network beamformer 156 may be implemented using a GPU, FPGA, ASIC, or other dedicated hardware (e.g., tensor processing unit) to perform the real-time computations associated with the neural network. In a prototype, the neural networks were implemented in Python using TensorFlow using the Adam optimizer with a single NVIDIA GeForce GTX 1080 Ti GPU, which has 11 GB of memory. The output from the neural network 156 is provided to an image processing component 158 which performs compression and persistence, resulting in a final diagnostic image which is presented to a medical professional on an image display 160.

We performed hyperparameter tuning of the learning rates, batch size, and both $l_1$ and $l_2$ regularization of filter weights to achieve optimal performance using an independent validation dataset that was separate from all other datasets. The final hyperparameters used are tabulated in Table 2.

TABLE 2

Network Training Hyperparameters

| Hyperparameter | Value |
| --- | --- |
| Learning Rate | $1 \times 10^{-4}$ |
| Filter $l_1$ Regularization | $1 \times 10^{-3}$ |

TABLE 2-continued

Network Training Hyperparameters

| Hyperparameter | Value |
| --- | --- |
| Filter $l_2$ Regularization | $1 \times 10^{-3}$ |
| Batch Size | 128 |

Neural Network Training and Analysis

Neural network training performance was analyzed as a function of training objective. A network with 16 convolution blocks and 32 filters per layer was trained to minimize either $\mathcal{L}^*_{l_1}$, $\mathcal{L}^*_{l_2}$, $\mathcal{L}^*_{MS\text{-}SSIM}$, or a mixture of $l_1$ and MS-SSIM, defined as:

$$\mathcal{L}^*_{Mix}(y,\hat{y}) = \mathcal{L}^*_{l_1}(y,\hat{y}) + \beta \mathcal{L}^*_{MS\text{-}SSIM}(y,\hat{y}), \quad (25)$$

where β was set heuristically to 200 to equalize the contributions of each loss function. Speckle reduction was evaluated on a validation dataset consisting of 32 new Field II Pro simulations, also based on photographs. Performance was quantified using the $\mathcal{L}^*_{l_1}$, $\mathcal{L}^*_{l_2}$, and $\mathcal{L}^*_{MS\text{-}SSIM}$ loss functions. Similarly, speckle reduction performance was also analyzed as a function of depth using networks with 2, 4, 8, or 16 blocks and 32 filters per layer, as well as networks with 16 blocks and 4, 8, 16, or 32 filters per layer, where all of the networks were trained to minimize $\mathcal{L}^*_{Mix}$. Finally, performance was compared with and without concatenating a B-mode image after the M-th convolution block.

Testing of Speckle Reduction Methods

All testing was performed using a neural network with a depth of 16 blocks, a width of 32 filters, and trained to minimize the $\mathcal{L}^*_{Mix}$ loss function for 30 training epochs unless otherwise indicated. The speckle reduction performance of the network was compared against those of receive spatial compounding and optimized Bayesian nonlocal means (OBNLM). Spatial compounding was implemented on receive by performing DAS beamforming and envelope detection independently on four non-overlapping subapertures and summing the result. The OBNLM algorithm was applied to images that were beamformed according to equation (1) using the publicly available MATLAB implementation provided by the authors of this algorithm. The default parameter values provided by the authors were used (M=7, α=3, h=0.7).

Simulation, phantom, and in vivo test datasets were used to evaluate beamforming performance. A simulation test dataset was obtained with Field II Pro with the same imaging configuration as the training dataset. Hypoechoic cylindrical cysts with diameters of 1 mm and 3 mm and contrasts of −20 dB and −6 dB were centered at the elevation focus of 2 cm depth. The full synthetic aperture set of channel signals was retrospectively focused into a 1 cm×1 cm pixel region also centered at the elevation focus, and the channels were delay-and-summed into 16 subaperture IQ signals. The simulated results were assessed using the $\mathcal{L}^*_{l_1}$, $\mathcal{L}^*_{l_2}$, and $\mathcal{L}^*_{M\text{-}SSIM}$ loss functions, as well as contrast, CNR, and SNR.

Generalizability from simulations to real-world ultrasound data was tested on a CIRS Model 040GSE calibrated phantom imaged using a Verasonics Vantage 256 research scanner with an L12-3v linear array transducer. Single element transmissions at 6 MHz sampled at 24 MHz were used to obtain a full synthetic transmit aperture for dynamic focusing on both transmit and receive. The channel data were focused into a pixel grid of 4 cm in depth and 2 cm in width, with a pixel spacing of λ/2 in both dimensions. Transmit and receive aperture growth were applied to achieve an f-number of 2. The phantom images were evaluated using contrast, CNR, and SNR.

Generalizability to clinical imaging conditions was assessed in vivo in the kidney of a healthy 58-year-old male volunteer and in the liver of a 68-year-old female who had a focal lesion with a surrounding fluid capsule. Channel datasets were acquired with a modified Siemens S2000 scanner using a Siemens 4C1 transducer. Pulse-inversion harmonic imaging was performed using focused transmissions at 1.82 MHz. Due to technical limitations, the channel signals were obtained for only 64 (out of 192) elements in a sector of 54 (out of 192) beams. The remaining beams were acquired using the full aperture using conventional DAS. The 64 receive channel signals were beamformed into 16 subaperture signals prior to being input into the neural network. For this particular dataset only, a partially-trained network (15 epochs rather than 30) was used to evaluate speckle reduction to avoid overfitting. Image quality was assessed using contrast, CNR, and SNR of the liver lesion vs. the surrounding fluid, with the ROIs selected to obtain a large region of speckle while avoiding obvious and significant changes in underlying echogenicity.

Neural Network Training and Analysis

Figure 2A:
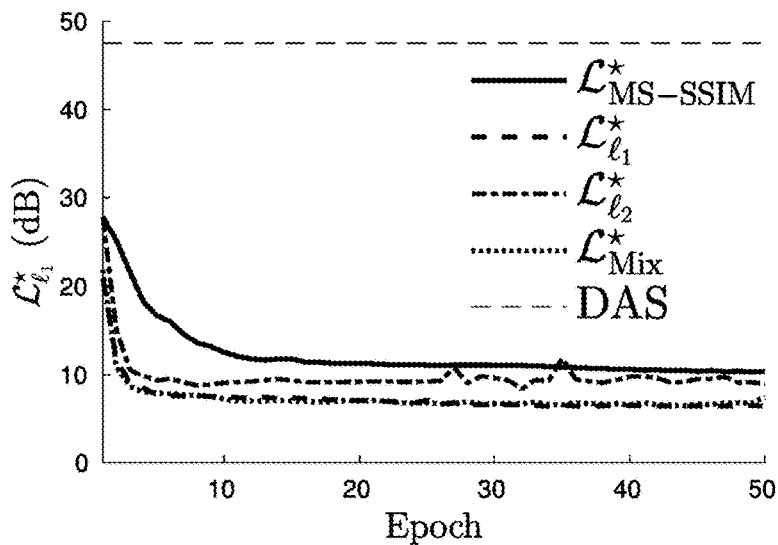
FIGS. 2A-C are graphs of validation losses versus network training objectives for different loss functions, according to an embodiment of the invention, where performance was measured using the (FIG. 2A) $\mathcal{L}^*_{l_1}$, (FIG. 2B) $\mathcal{L}^*_{l_2}$, and (FIG. 2C) $\mathcal{L}^*_{MS-SSIM}$ losses after each training epoch, as measured on the validation dataset.
Figure 2B:
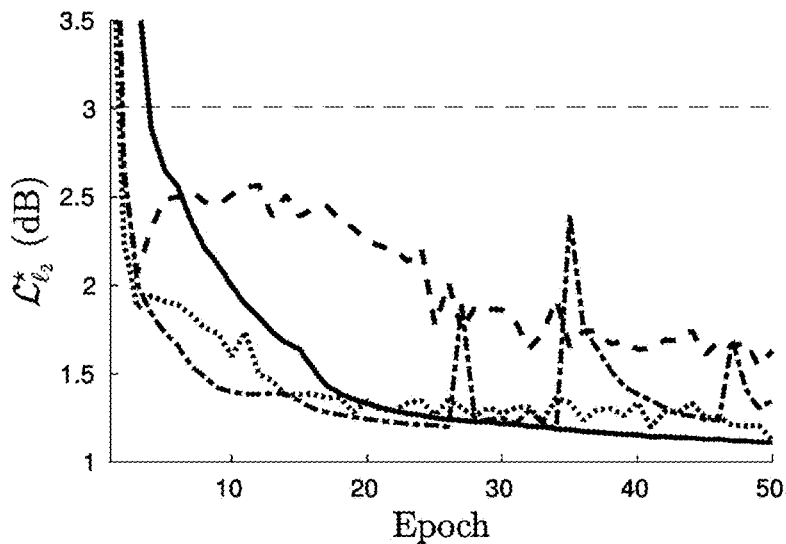
Figure 2C:
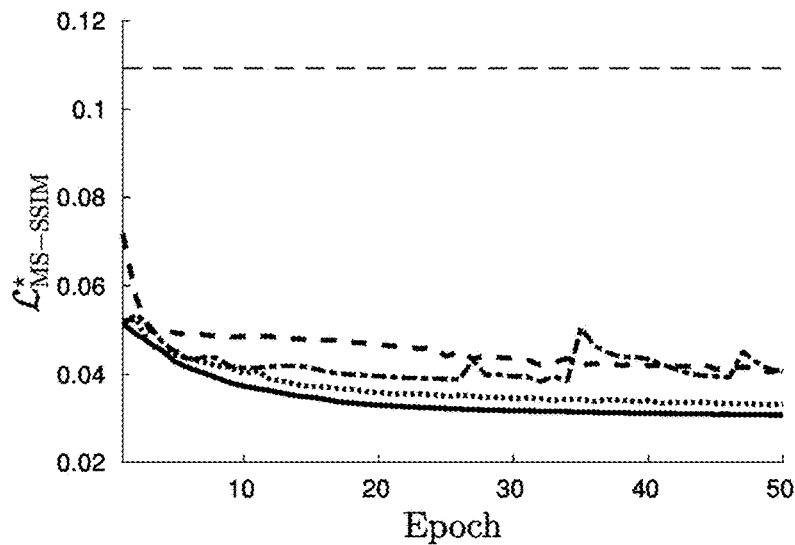
Figure 3A:
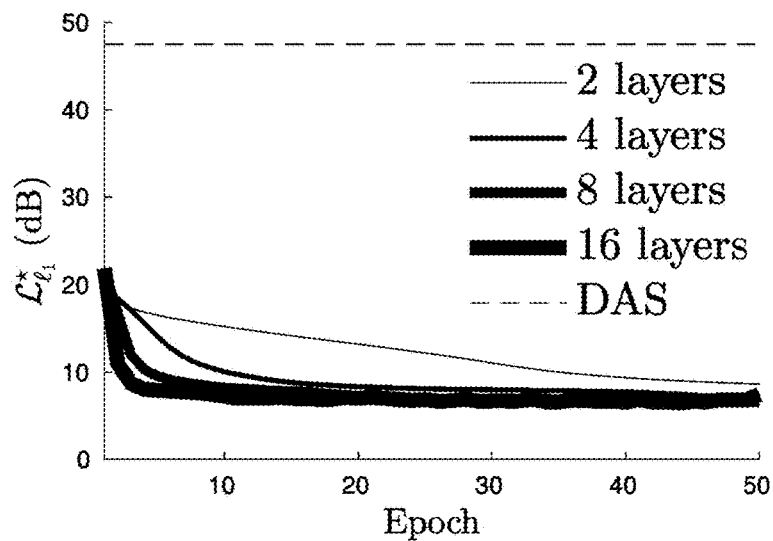
FIGS. 3A-F are graphs of validation losses versus network architecture, where
Figure 3B:
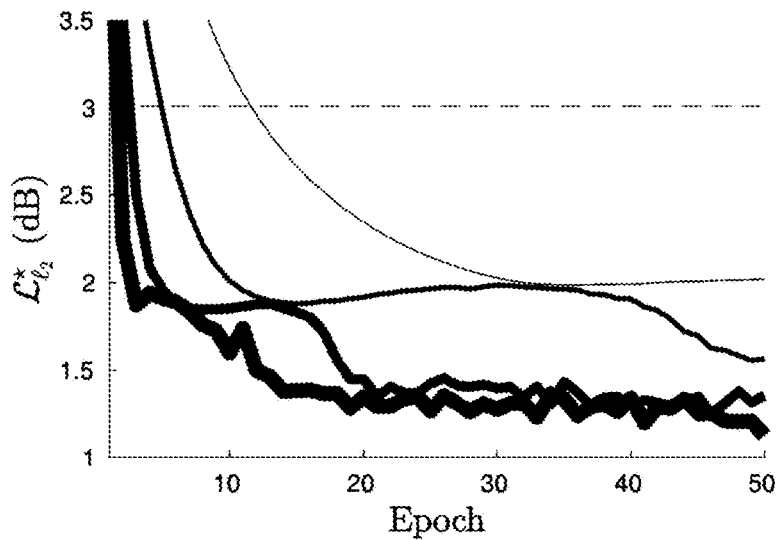
Figure 3C:
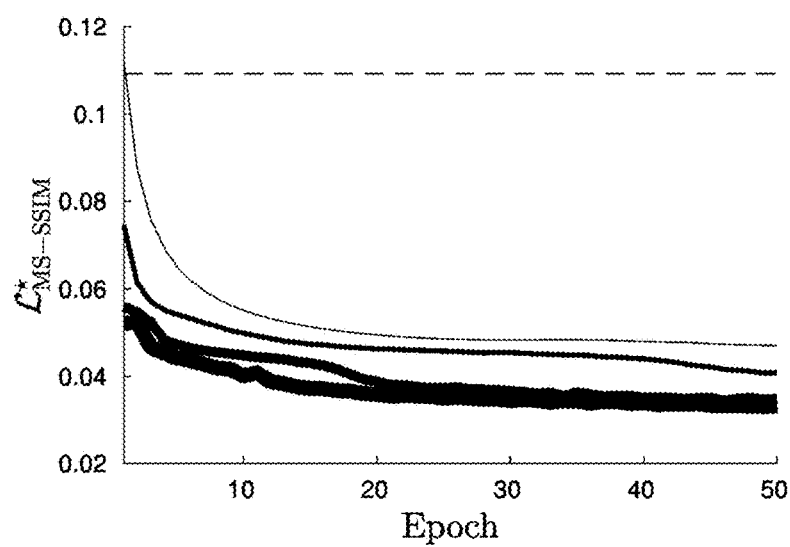
Figure 3D:
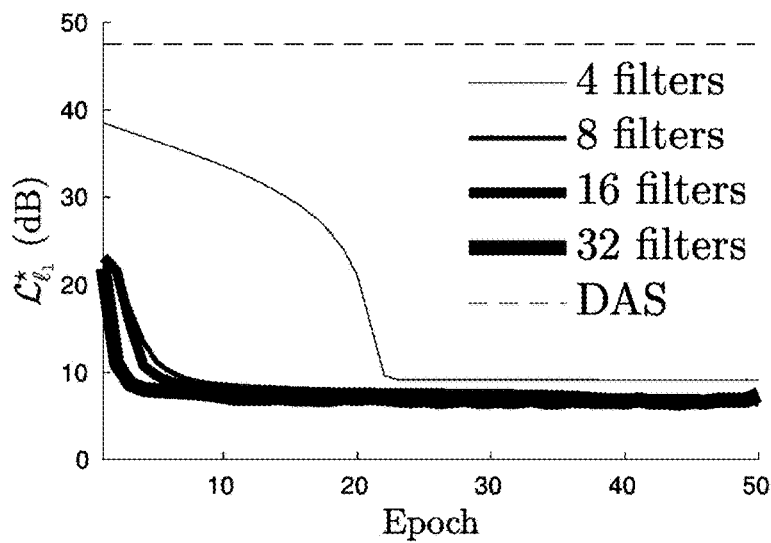
Figure 3E:
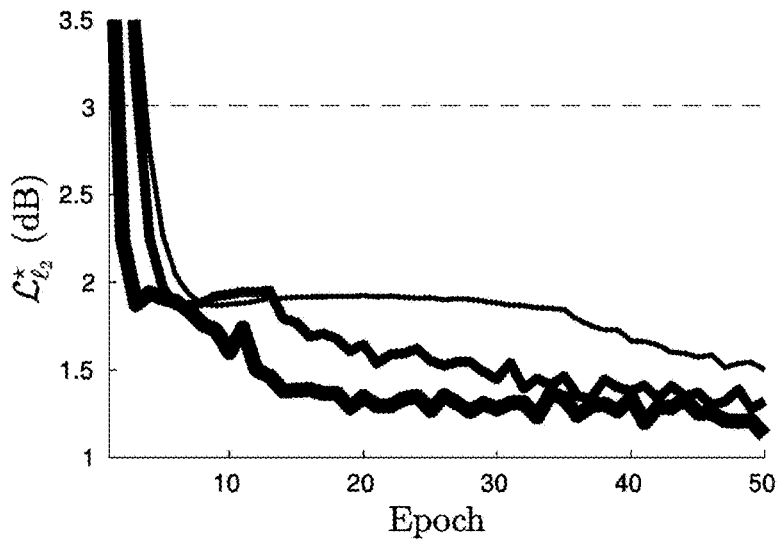
Figure 3F:
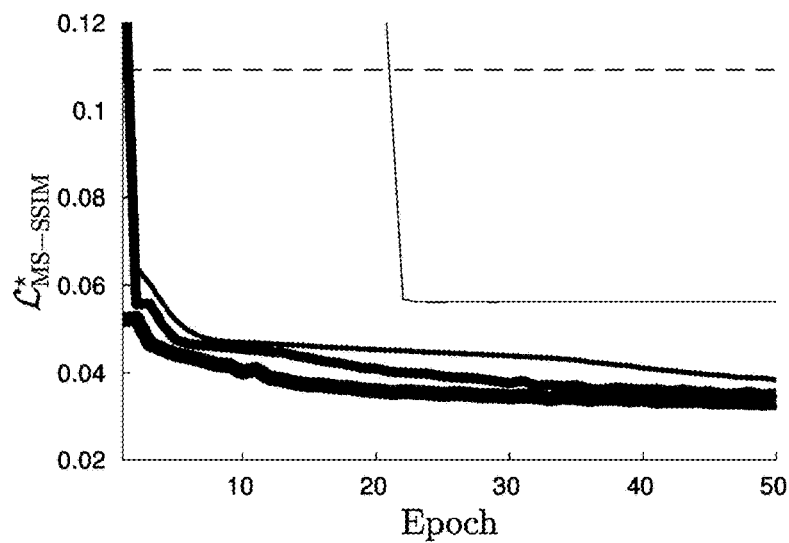

FIGS. 2A-C plots the $\mathcal{L}^*_{l_1}$, $\mathcal{L}^*_{l_2}$, and $\mathcal{L}^*_{MS\text{-}SSIM}$ validation losses of neural networks over 50 training epochs for several training objectives, as computed on the validation dataset. The neural network was trained to minimize $\mathcal{L}^*_{MS\text{-}SSIM}$ (solid), $\mathcal{L}^*_{l_1}$ (dashed), $\mathcal{L}^*_{l_2}$ (dot-dashed), or $\mathcal{L}^*_{Mix}$ (dotted). Performance was measured using the $\mathcal{L}^*_{l_1}$ (FIG. 2A), $\mathcal{L}^*_{l_2}$ (FIG. 2B), and $\mathcal{L}^*_{MS\text{-}SSIM}$ (FIG. 2C) losses after each training epoch, as measured on the validation dataset. The losses of the DAS reconstruction (thin line) are shown for reference. The networks trained to minimize $\mathcal{L}^*_{l_1}$ and $\mathcal{L}^*_{Mix}$ were found to yield the lowest $\mathcal{L}^*_{l_1}$ losses. The networks trained to minimize $\mathcal{L}^*_{MS\text{-}SSIM}$ and $\mathcal{L}^*_{Mix}$ yielded the lowest $\mathcal{L}^*_{MS\text{-}SSIM}$ and $\mathcal{L}^*_{l_2}$ losses. Minimizing $\mathcal{L}^*_{l_2}$ resulted in unstable performance, with erratic increases in all three losses occurring partway through training. Minimizing $\mathcal{L}^*_{Mix}$ resulted in fast and smooth reduction in all three losses.

FIGS. 3A-F shows the validation losses as a function of network depth and width for a network trained to minimize $\mathcal{L}^*_{Mix}$ on the validation dataset. Given a fixed width of 32 filters, deeper networks converged to lower $\mathcal{L}^*_{l_1}$, $\mathcal{L}^*_{l_2}$, and $\mathcal{L}^*_{MS\text{-}SSIM}$ losses after 50 epochs, and approached these values more rapidly as well. Similar results were observed when fixing the network depth to 16 layers and increasing the width. With the exception of the network with a width of 4 filters, all networks outperformed DAS beamforming by the $\mathcal{L}^*_{l_1}$, $\mathcal{L}^*_{l_2}$, and $\mathcal{L}^*_{MS\text{-}SSIM}$ metrics. In general, it was observed that the deeper and wider networks trained more quickly and resulted in lower $\mathcal{L}^*_{l_1}$, $\mathcal{L}^*_{l_2}$, and $\mathcal{L}^*_{MS\text{-}SSIM}$ losses, as measured on the validation set.

Figure 4A:
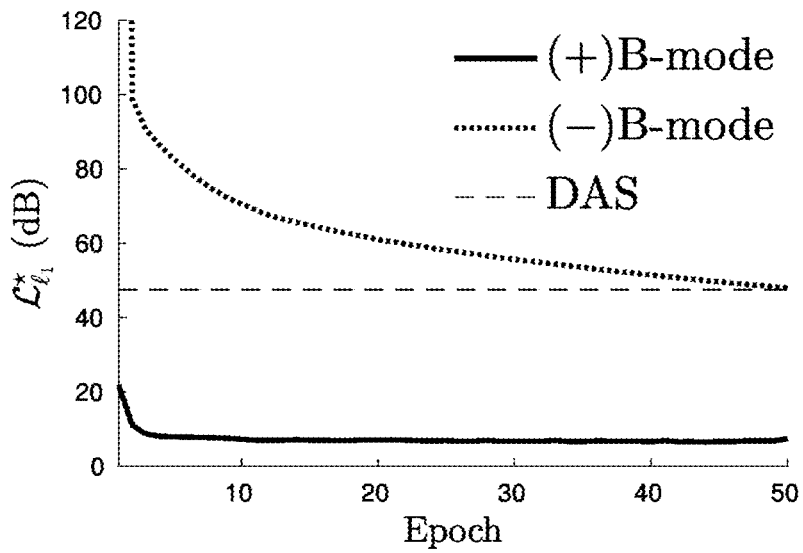
FIGS. 4A-C are graphs of validation losses with (+) and without (−) a concatenated B-mode (i.e., summed and envelope detected) image after the M-th convolution block, measured by (FIG. 4A) $\mathcal{L}^*_{l_1}$, (FIG. 4B) $\mathcal{L}^*_{l_2}$, and (FIG. 4C) $\mathcal{L}^*_{MS-SSIM}$, according to an embodiment of the invention.
Figure 4B:
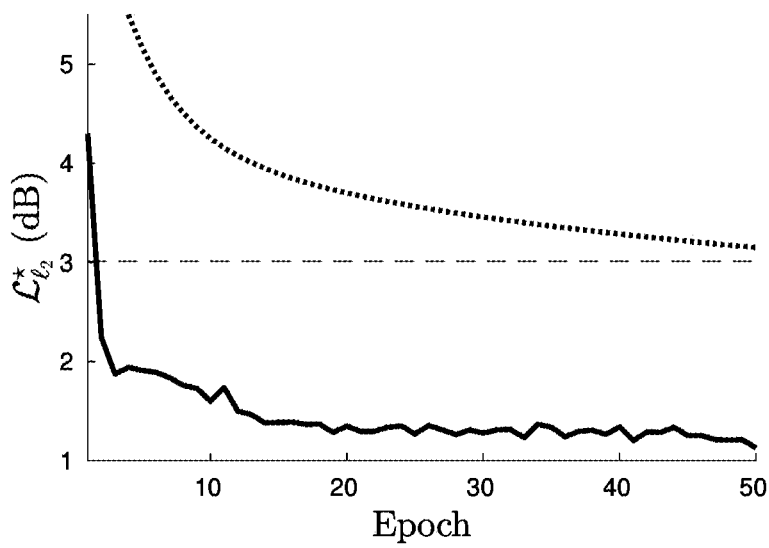
Figure 4C:
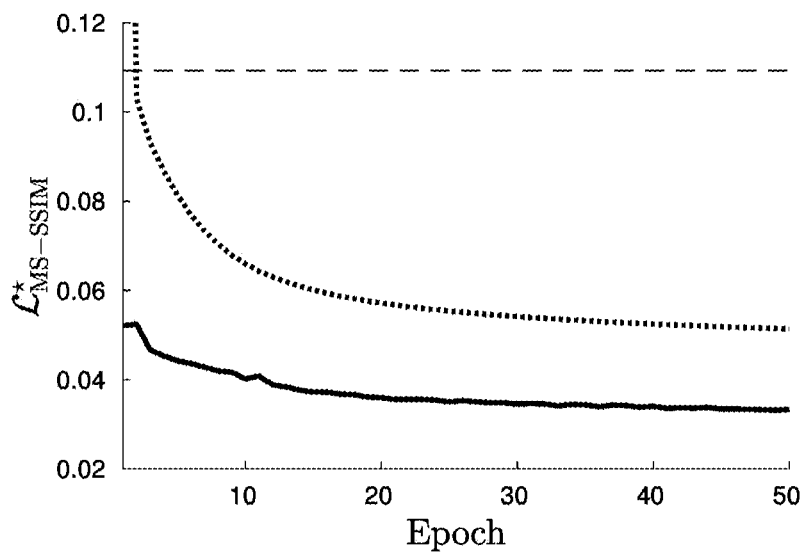

FIGS. 4A-C plots the same validation losses for networks trained to minimize $\mathcal{L}^*_{Mix}$ with and without a concatenated B-mode image after the M-th convolutional block. The network with B-mode concatenation (solid) significantly outperformed the network without B-mode (dotted) as measured by $\mathcal{L}^*_{l_1}$ (FIG. 4A), $\mathcal{L}^*_{l_2}$ (FIG. 4B), and $\mathcal{L}^*_{MS\text{-}SSIM}$ (FIG. 4C). The network without B-mode outperformed DAS beamforming in only $\mathcal{L}^*_{MS\text{-}SSIM}$.

Though not plotted here, the training errors closely followed the trends of the validation errors in all cases in FIGS. 2A-C, FIGS. 3A-F, and FIGS. 4A-C, indicating that the networks were not overfitting to the training data.

Image Resolution

The FWHM of the LSF was used to measure the azimuthal resolution of each imaging method. The resolutions were found to be: $DAS_{FWHM}=0.132$ mm; $SC_{FWHM}=0.156$ mm; $OBNLM_{FWHM}=0.186$ mm; and $NN_{FWHM}=0.129$ mm, where the neural network was evaluated after being trained to minimize $\mathcal{L}^*_{Mix}$ for 30 epochs.

Cyst Simulation Results

Figure 5:
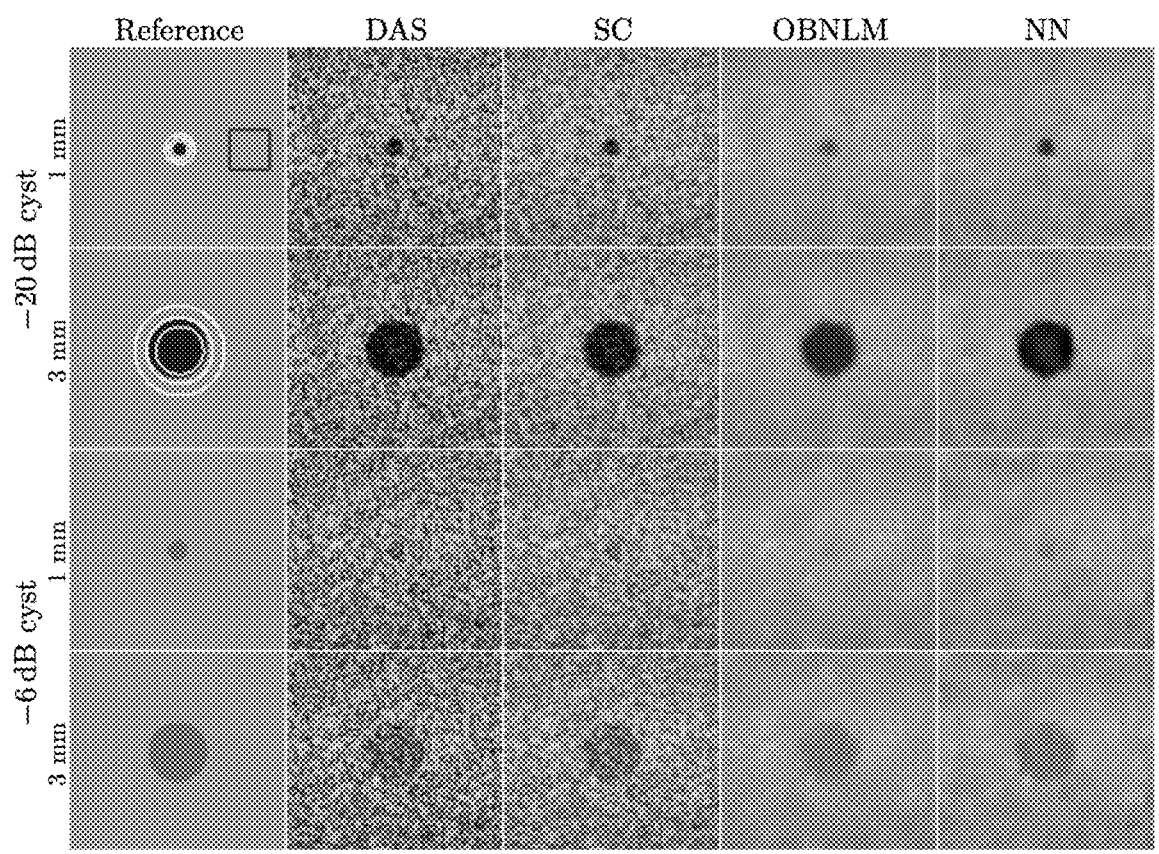
FIG. 5 is an image grid showing Field II simulation images of cysts reconstructed using DAS, spatial compounding (SC), OBNLM, and the neural network (NN) according to an embodiment of the present invention. The top two rows show 1 mm and 3 mm −20 dB cysts, while the bottom two rows show the same for −6 dB cysts. The ground truth echogenicity reference is shown in the leftmost column, overlaid with the circular ROIs used for contrast measurements and the square ROI used for SNR measurement.

Images reconstructed using DAS, spatial compounding, OBNLM, and the neural network are pictured in FIG. 5, along with the reference images. Image quality metrics for each method in the test dataset of simulated cysts are presented in Table 3. Overall, the $\mathcal{L}^*_{l_1}$ and $\mathcal{L}^*_{l_2}$ losses in the relatively simple test set were lower than those found in the more complex validation set used in FIGS. 2A-C and FIGS. 3A-F, which was composed of photographic images. DAS accurately reproduced contrast in the 3 mm lesions, and was within 3 dB for the 1 mm lesions.

Qualitatively, spatial compounding exhibited moderate speckle reduction while preserving

TABLE 3

Test Dataset 1: Cyst Simulation Reconstruction Metrics

| Target | Metric | DAS | SC | OBNLM | NN* |
|---|---|---|---|---|---|
| All simulations | $\mathcal{L}_{l_1}^\star$(dB) | 28.09 | 12.49 | 4.17 | 4.88 |
| All simulations | $\mathcal{L}_{l_2}^\star$(dB) | 2.84 | 1.13 | 0.20 | 0.18 |
| All simulations | $\mathcal{L}_{MS\text{-}SSIM}^\star$ | 0.108 | 0.050 | 0.005 | 0.005 |
| −20 dB 1 mm cyst | Contrast | −17 dB | −15 dB | −7 dB | −13 dB |
| −20 dB 3 mm cyst | Contrast | −20 dB | −19 dB | −18 dB | −20 dB |
| −6 dB 1 mm cyst | Contrast | −7 dB | −7 dB | −2 dB | −3 dB |
| −6 dB 3 mm cyst | Contrast | −6 dB | −6 dB | −5 dB | −5 dB |
| −20 dB 1 mm cyst | CNR | −1.8 | −2.2 | −3.6 | −4.6 |
| −20 dB 3 mm cyst | CNR | −1.6 | −2.2 | −6.5 | −6.7 |
| −6 dB 1 mm cyst | CNR | −1.0 | −1.2 | −2.4 | −2.8 |
| −6 dB 3 mm cyst | CNR | −0.8 | −1.1 | −3.1 | −2.7 |
| Background | SNR | 1.87 | 2.50 | 11.16 | 11.00 |

*Trained to minimize $\mathcal{L}_{Mix}^\star$ for 30 epochs contrast and resolution throughout the images. Spatial compounding approximately halved the test loss values. The contrast measurements of the −20 dB cyst were slightly worse than DAS, but the SNR was improved by 34%, resulting in overall improvements in CNR. OBNLM applied considerable smoothing to the speckle (497% SNR increase) and produced the lowest $\mathcal{L}^*_{l_1}$ losses of all methods. However, OBNLM exhibited a visible loss in resolution, resulting in significantly degraded contrasts in the 1 mm cysts. Note that speckle artifacts are still visible in the background texture of the images, indicating that the smoothing parameter of OBNLM was set conservatively. We observed that relaxing the smoothing parameter resulted in worsened speckle texture without a gain in resolution, while more aggressive smoothing eliminated these artifacts but led to a further loss in resolution (not pictured). Both OBNLM and the neural network resulted in a 20-fold reduction in $\mathcal{L}^*_{MS\text{-}SSIM}$ losses from DAS. The neural network additionally had the lowest $\mathcal{L}^*_{l_2}$ loss of all methods, and increased the speckle SNR by 488%. The neural network resulted in higher CNR than DAS, SC, and OBNLM in all cysts except for the −6 dB 3 mm cyst.

Phantom Imaging

TABLE 4

Test Dataset 2: Phantom Reconstruction Metrics

| Target | Metric | DAS | SC | OBNLM | NN* |
|---|---|---|---|---|---|
| −12 dB cyst | Contrast | −10 dB | −10 dB | −9 dB | −11 dB |
| −6 dB cyst | Contrast | −5 dB | −5 dB | −5 dB | −5 dB |
| +6 dB cyst | Contrast | +2 dB | +2 dB | +2 dB | +2 dB |
| +12 dB cyst | Contrast | +5 dB | +5 dB | +5 dB | +6 dB |
| −12 dB cyst | CNR | −1.2 | −1.6 | −2.9 | −2.3 |
| −6 dB cyst | CNR | −0.8 | −1.1 | −2.2 | −1.6 |
| +6 dB cyst | CNR | +0.2 | +0.5 | +0.7 | +0.8 |
| +12 dB cyst | CNR | +0.7 | +1.2 | +2.9 | +2.2 |
| Background | SNR | 1.90 | 2.57 | 11.60 | 7.73 |

*Trained to minimize $\mathcal{L}_{Mix}^*$ for 30 epochs

Figure 6A:
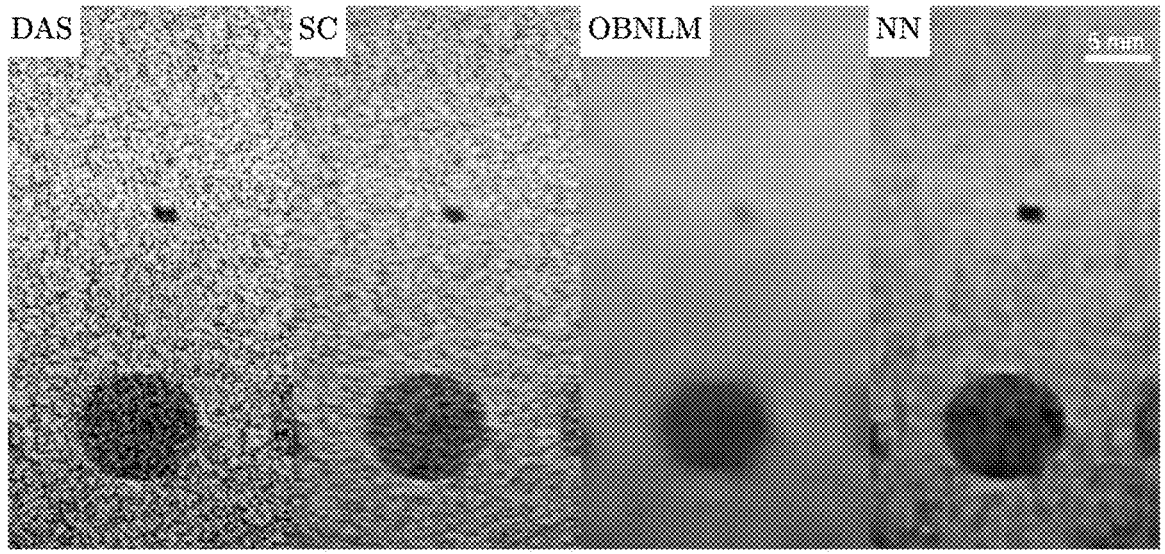
FIG. 6A-B show phantom images reconstructed using DAS, spatial compounding, OBNLM, and the neural network according to an embodiment of the invention. Each image is normalized and displays 40 dB of dynamic range.
Figure 6B:
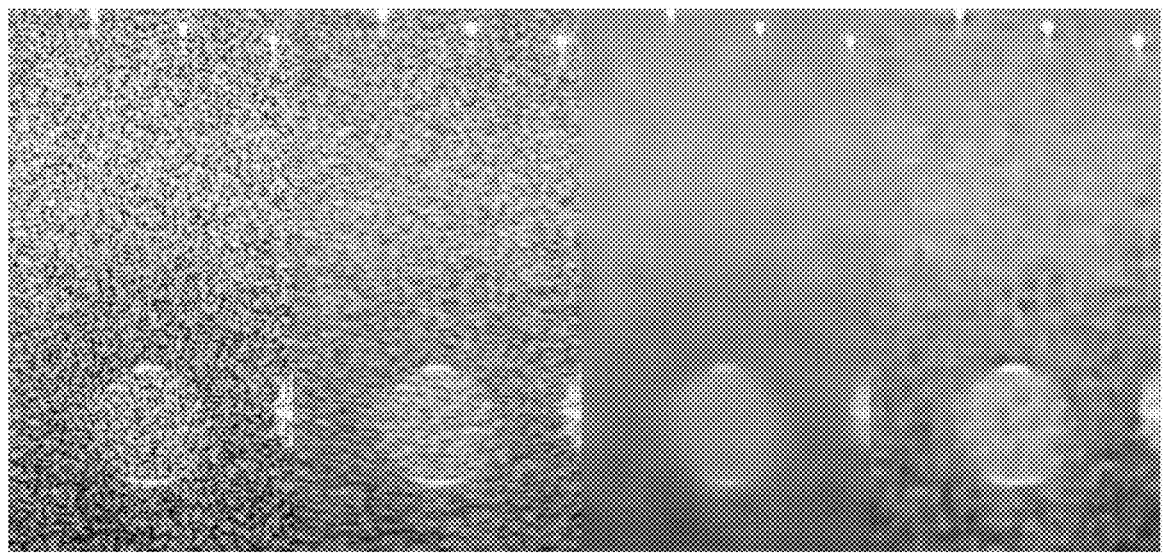

Images of the tissue mimicking phantom are shown in FIG. 6A-B. The images in FIG. 6A show a −12 dB hypoechoic cyst and a smaller anechoic cyst, while the images in FIG. 6B show a +12 dB hyperechoic cyst and point targets at the top. Contrasts and CNRs for −12 dB, −6 dB (not pictured), +6 dB (not pictured), and +12 dB 8 mm cysts are included in Table 4, along with the speckle SNR. In the DAS images, some mild signal attenuation was visible in the lower half of each image resulting in darker textures. Additionally, both the +6 dB and +12 dB hyperechoic cysts exhibited unexpectedly low contrasts of +1 dB and +5 dB in the DAS image. The DAS speckle SNR of 1.90 matched the classical prediction. Spatial compounding preserved cyst contrasts while smoothing the speckle texture, improving the SNR by 35%. Over the four cysts, spatial compounding improved the CNR on average by 67%. The OBNLM technique significantly smoothed the speckle and preserved the point targets, though the lateral edges of the hypoechoic and anechoic cysts were blurred. Overall, OBNLM improved SNR by 511% and CNR by 211%.

The neural network demonstrated excellent speckle reduction, improving the SNR by 306% over DAS. The contrasts were also preserved, resulting in higher CNRs than both DAS and spatial compounding in all cases. The neural network images also presented sharp high-resolution outlines around the −12 dB and anechoic cysts, while the outlines around the +12 dB cyst were less sharp. The images were subject to similar attenuation effects as DAS. Some dark textures and structures were visible around the deep cysts, and appeared to correspond to the speckle textures in the DAS image. The three point targets near the transducer surface were also preserved, but were slightly enlarged.

In Vivo Imaging

TABLE 5

Test Dataset 3: In Vivo Reconstruction Metrics

| Target | Metric | DAS | SC | OBNLM | NN* |
|---|---|---|---|---|---|
| Liver lesion | SNR | 1.63 | 2.62 | 1.83 | 3.09 |
| Surrounding fluid | Contrast | −20 dB | −18 dB | −19 dB | −22 dB |
| Surrounding fluid | CNR | −1.5 | −2.3 | −1.6 | −2.8 |

*Trained to minimize $\mathcal{L}_{Mix}^*$ for 15 epochs

Figure 7A:
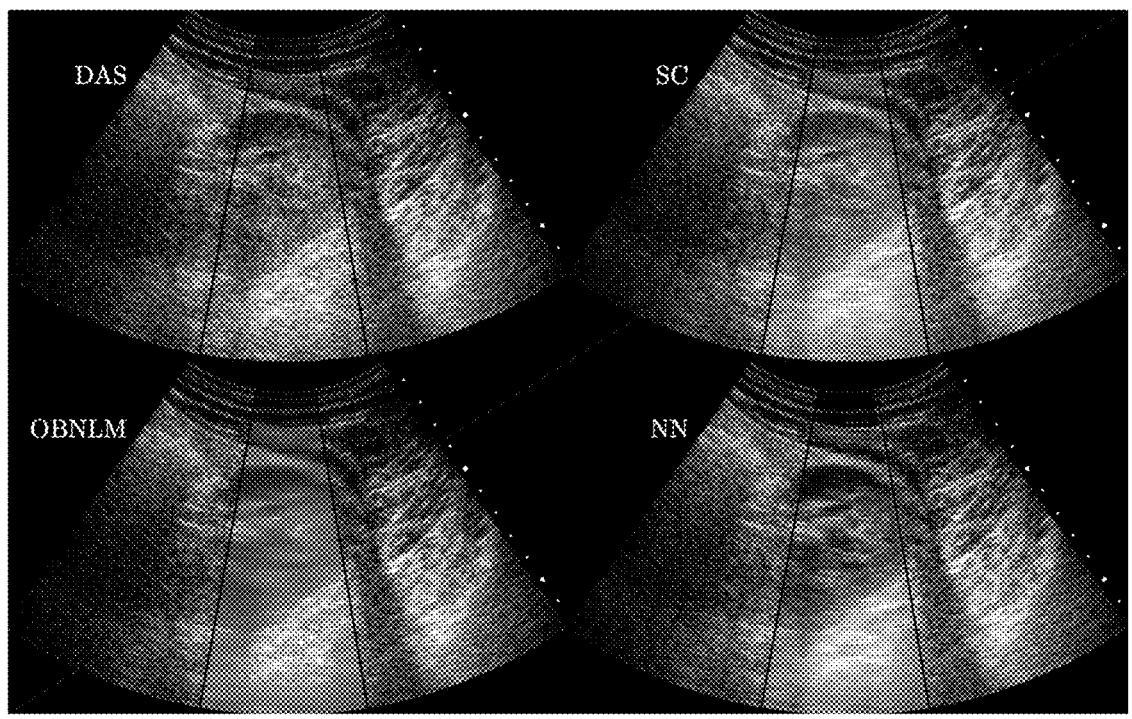
FIGS. 7A-B are harmonic B-mode images of a kidney (FIG. 7A) and a complex focal lesion surrounded by an anechoic fluid (FIG. 7B). The center sectors (bounded with black lines) were reconstructed using DAS, spatial compounding, OBNLM, and the neural network according to an embodiment of the invention, and are overlaid on the full B-mode sector scan. The tick marks show 1 cm spacing. Each image displays 50 dB of dynamic range.
Figure 7B:
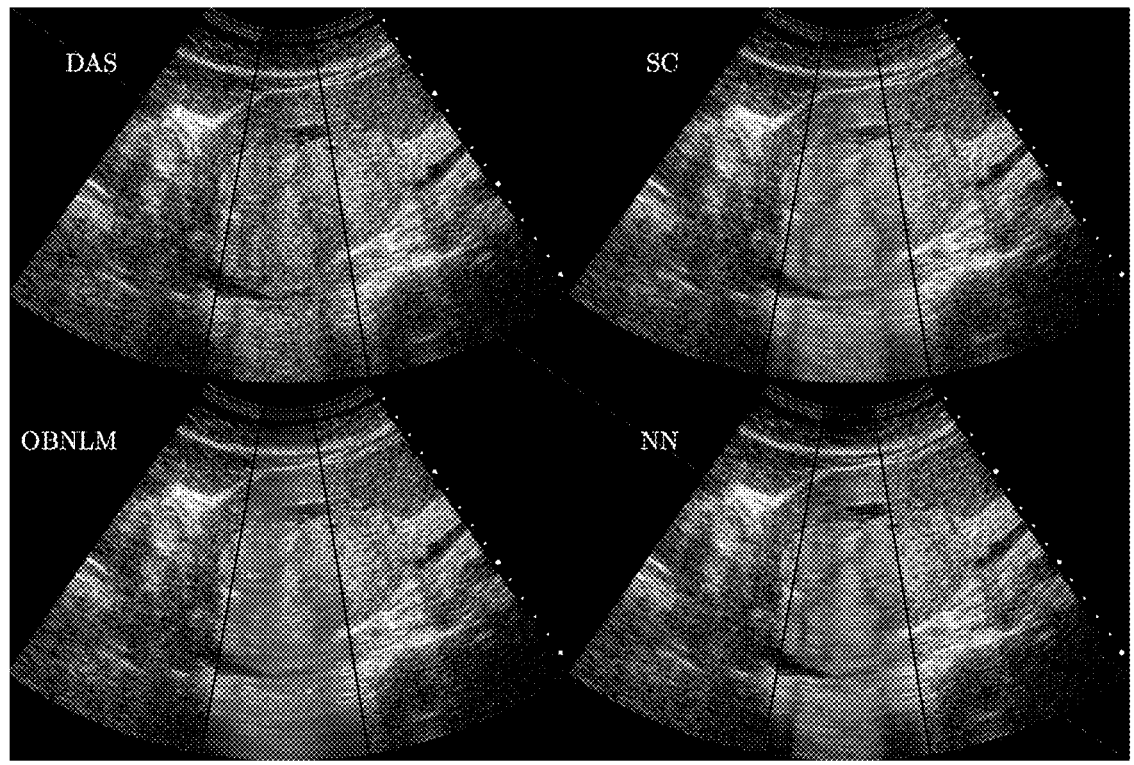
Figure 7C:
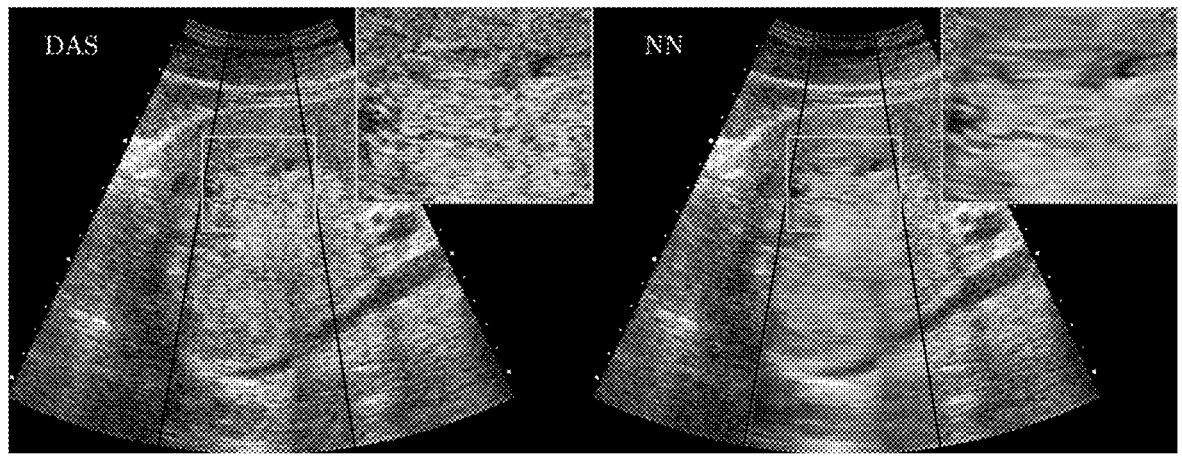
FIGS. 7C-D are two additional views of the same kidney and focal liver lesion of FIGS. 7A-B, with zoomed insets showing closer detail. These figures show substantial speckle reduction with the preservation of fine details and structures according to an embodiment of the present invention.
Figure 7D:
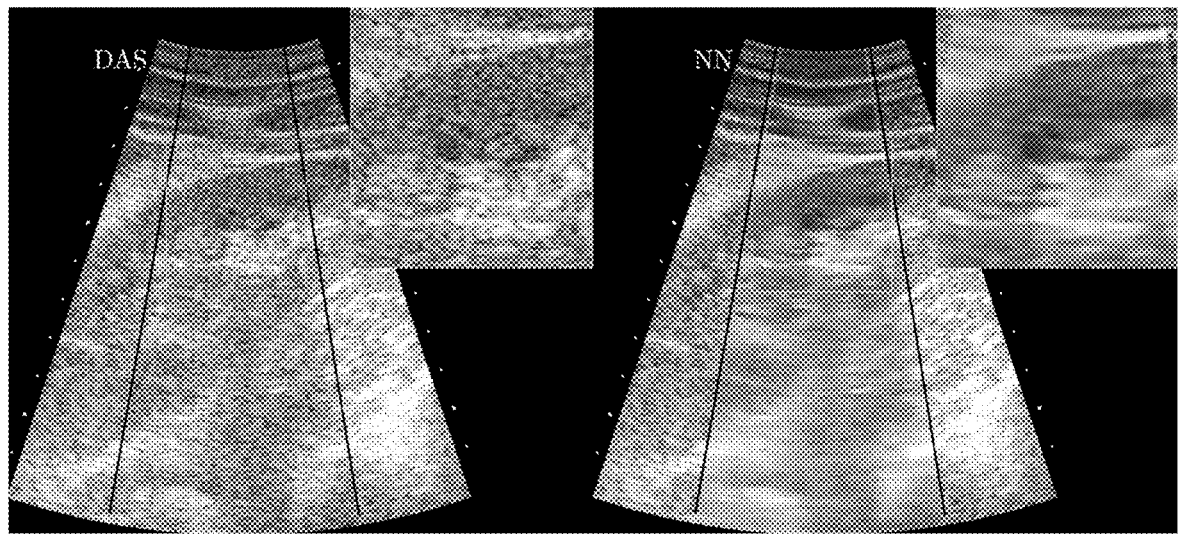

FIGS. 7A-B are In vivo harmonic B-mode images of a kidney (FIG. 7A) and a complex focal liver lesion surrounded by an anechoic fluid (FIG. 7B). Image quality metrics are included in Table 5. Both spatial compounding images exhibited significantly reduced speckle with marginal losses in resolution in both images. However, there was a visible loss in contrast throughout. The effects combined for a net increase in SNR of 60% and CNR of 56%. OBNLM preserved bright granular structures throughout the brighter regions of tissue but applied aggressive smoothing in darker image regions with gradual changes in echogenicity. Overall, OBNLM increased SNR and CNR over DAS by 12% and by 10%, respectively. The neural network significantly reduced speckle while improving contrast. The structures within the kidney and the lobes of the liver lesion were well-preserved, and the clutter within the surrounding fluid of the liver lesion was reduced. Shadowing effects visible in DAS were preserved in the neural network images. Overall, the SNR and CNR was increased by 90% and 93% over DAS, respectively. FIGS. 7C-D are two additional views of the same kidney and focal liver lesion, with zoomed insets showing closer detail. These figures show substantial speckle reduction with the preservation of fine details and structures.

In conclusion, the neural network was able to estimate the true echogenicity more accurately than DAS and spatial compounding, as measured by the $\mathcal{L}^*_{l_1}$, $\mathcal{L}^*_{l_2}$, and $\mathcal{L}^*_{MS\text{-}SSIM}$ losses. The neural network beamformer outputted a homogeneous response in regions of constant echogenicity while mostly preserving the shapes of the cysts.

The neural network is notably trained entirely in silico and can generalize to real-world imaging, including in vivo. The neural network reduced speckle more effectively than receive-only spatial compounding in both the phantom and in vivo. The in vivo results were particularly remarkable considering that the training and test datasets were acquired with a different transducer (L12-3v at 8 MHz vs. 4C1 at 3.6 MHz), imaging configuration (linear vs. curvilinear), and transmit focusing scheme (full synthetic aperture vs. focused transmits), and additionally contained reverberation clutter and inhomogeneities in sound speed leading to focusing errors. The robust performance may be attributed to the wide variety of speckle patterns observed in the randomly generated training dataset. By randomly selecting the physical width, height, and position of each 64×64 pixel training patch, the networks were provided with diverse examples of speckle shapes, which was effectively equivalent to providing the networks with diverse examples of point spread functions. Although the emphasis of this work was placed on the task of estimating echogenicity, the training dataset also contained simulated examples of both white electronic and band-limited acoustic noise, which may have further aided the networks in generalizing to real data.

The resolution measurements show that the neural network preserves resolution in speckle targets, unlike spatial compounding and OBNLM. Consequently, the network preferably should be trained with not only diffuse scatterers but also sharp point targets. In addition, the training data should be tailored to match the specific imaging parameters (e.g., transducer geometry, frequency, imaging depth, and focusing configuration) of the anticipated applications, including using appropriate speckle-to-pixel size ratios and pixel spacing. In some embodiments, performance may also be improved by explicitly incorporating prior knowledge about the physics of ultrasound beamforming. For example, full spatial compounding on both transmit and receive is known to improve the edge definition of specular targets by interrogating the targets from multiple angles; a hybridized approach with spatial compounding of neural network-beamformed images could potentially yield better visibility of specular boundaries while reducing speckle.

Overall, the neural networks trained quickly and robustly. All of the presented networks were trained in under 30 minutes on a workstation equipped with a single NVIDIA GeForce GTX 1080 Ti GPU, and could process a single image frame in under 30 ms. The networks converged to nearly identically performing states for random filter weight initializations, indicating good repeatability. The networks were also observed to be insensitive to hyperparameters such as convolution filter weight regularization, which was set to values ranging from $10^{-4}$ to $10^{-1}$ with marginal differences in output.

Deeper and wider networks can represent a broader range of functions, a property called expressive power. The benefits of expressive power were shown in FIGS. 3A-F, where the deeper and wider networks were able to lower the $\mathcal{L}^*_{l_1}$, $\mathcal{L}^*_{l_2}$, and $\mathcal{L}^*_{MS\text{-}SSIM}$ losses in the validation dataset more rapidly and to a lower overall value. However, expressive networks are also more prone to overfitting the training data and generalizing poorly to new data. Overfitting can be detected by observing an increase in validation loss during training, and is often caused by a dataset that is too small relative to the expressive power of the network. This type of overfitting was not exhibited in FIGS. 3A-F, which showed stable improvements in validation loss with more training epochs, suggesting that our training dataset was large enough.

A second form of overfitting can occur when the training dataset distribution differs from the testing dataset distribution, as was the case in this study. The simulated training dataset was obtained using significantly different configurations and noise conditions from the phantom and in vivo test data. Unfortunately, the validation loss could not be used to observe this type of overfitting because the ground truth was unavailable in the phantoms and in vivo. Instead, we qualitatively observed that a network trained for 30 epochs led to less speckle reduction and an over-emphasis of small speckle troughs in vivo as compared to a network trained for just 15 epochs. This suggests that the second form of overfitting occurred, with the network learning to recognize features in the simulated environment that were not present in the in vivo data. Accordingly, in some embodiments, generalizability to in vivo imaging is improved by training the network with more realistic simulations that model full wave propagation to include the effects of phase aberration, reverberation, and attenuation, as well as diffuse, specular, and point reflectors.

In addition to using a new dataset and reducing the number of training epochs, overfitting can be mitigated by employing regularization. We used the $l_1$- and $l_2$-norms of the filter weights to enforce smaller weights. Furthermore, we utilized a priori knowledge that the backscatter from diffuse scatterers has high correlation coefficients between neighboring array elements to reduce the full 128 element array into 16 beamformed subapertures. Although motivated by computational constraints, subaperture beamforming effectively applied a regularization by reducing the expressivity of the network. More sophisticated forms of regularization, such as total variation, can be included to further reduce the impact of overfitting.

The invention claimed is:

1. A method for ultrasound image reconstruction using a convolutional neural network (CNN), the method comprising:
    (a) training the CNN with a dataset comprising simulated transducer array channel signals containing simulated speckle as inputs, and corresponding simulated speckle-free echogenicity estimates (B-mode images) as outputs; wherein the training uses a loss function involving a norm between estimated B-mode images and simulated speckle-free B-mode images; wherein the estimated B-mode images are estimated by the CNN from the simulated transducer array channel signals;
    (b) measuring real-time RF signals taken directly from ultrasound transducer array elements prior to summation;
    (c) preprocessing the measured real-time RF signals to apply time delays to focus the array at field points, and inputting the pre-processed measured real-time RF signals to the CNN;
    (d) processing by the CNN the pre-processed measured real-time RF signals to produce as output an estimated real-time B-mode image with reduced speckle.

2. The method of claim 1 wherein the loss function is a log-domain normalization-independent loss function.

3. The method of claim 1 wherein the loss function is a normalization-independent mixture of $l_1$ and multi-scale structural similarity losses.

4. The method of claim 1 wherein the CNN has 8 to 16 convolution blocks, wherein each of the convolution blocks has a 2D convolution, batch normalization, and a rectified linear unit.

5. The method of claim 1 wherein the CNN has 16 layers of convolution blocks and 32 filters per layer.

6. The method of claim 1 further comprising performing a conventional DAS envelope-detection reconstruction to generate a conventional B-mode image from the real-time RF signals, and concatenating the generated conventional B-mode image to an output of a block of the CNN.

7. The method of claim 1 wherein simulated transducer array channel signals are unfocused or focused channel signals.

8. The method of claim 1 wherein the input signals are modulated RF signals or demodulated baseband signals.

9. The method of claim 1 wherein the CNN concatenates the original input data to an intermediate hidden layer of the network.

10. The method of claim 1 wherein the CNN performs a multi-scale or multi-resolution processing of the data via striding or pooling.

11. The method of claim 1 wherein the CNN utilizes 3D convolutions.

* * * * *